(12) United States Patent
King et al.

(10) Patent No.: US 12,239,493 B2
(45) Date of Patent: Mar. 4, 2025

(54) METHODS AND DEVICES FOR MEDICAL DEVICE PLACEMENT

(71) Applicant: Medical AccuFix, LLC, Houston, TX (US)

(72) Inventors: Ray King, Houston, TX (US); Ashok Gowda, Houston, TX (US); Charles Houssiere, Houston, TX (US)

(73) Assignee: Medical AccuFix, LLC, Houston, TX (US)

(*) Notice: Subject to any disclaimer, the term of this patent is extended or adjusted under 35 U.S.C. 154(b) by 968 days.

(21) Appl. No.: 16/340,970

(22) PCT Filed: Oct. 12, 2017

(86) PCT No.: PCT/US2017/056387
§ 371 (c)(1),
(2) Date: Apr. 10, 2019

(87) PCT Pub. No.: WO2018/071702
PCT Pub. Date: Apr. 19, 2018

(65) Prior Publication Data
US 2019/0282320 A1     Sep. 19, 2019

Related U.S. Application Data

(60) Provisional application No. 62/407,472, filed on Oct. 12, 2016.

(51) Int. Cl.
*A61B 90/11*     (2016.01)
*A61B 17/84*     (2006.01)
(Continued)

(52) U.S. Cl.
CPC .......... *A61B 90/11* (2016.02); *A61B 17/8645* (2013.01); *A61B 17/8891* (2013.01);
(Continued)

(58) Field of Classification Search
CPC ...... A61B 2017/044; A61B 2017/0409; A61B 2017/0414; A61B 2017/0445;
(Continued)

(56) References Cited

U.S. PATENT DOCUMENTS

| 4,809,694 A | 3/1989 | Ferrara |
| 5,116,345 A | 5/1992 | Jewell et al. |

(Continued)

FOREIGN PATENT DOCUMENTS

| EP | 1016432 A2 | 7/2000 |
| EP | 2919686 A1 | 9/2015 |
| JP | 2008535544 A | 9/2008 |

*Primary Examiner* — Majid Jamialahmadi
(74) *Attorney, Agent, or Firm* — Equip LG; Christopher Quan

(57) ABSTRACT

The invention relates to a method and device for maintaining a separately-determined trajectory and securing an electrode or other such placed object through a bone, such as a skull, while also covering the aperture. The device includes a base and an engaging-disengaging butterfly with inner sleeve for temporary engagement of the base and sliding screwdriver for engaging the base or butterfly inner sleeve, depending upon desired function. The base's lower portion engages via threads the bone, while maintaining previously determined trajectory; the upper portion engages the butterfly to continue to maintain previously determined trajectory electrode trajectory; a feature grasps a passing electrode in a given position; the electrode grasp from the butterfly can be then released, the base screwed in to final position, and the butterfly disengaged by unscrewing it from the base.

16 Claims, 4 Drawing Sheets

(51) Int. Cl.
*A61B 17/86* (2006.01)
*A61B 17/88* (2006.01)
*A61B 90/14* (2016.01)
*A61N 1/05* (2006.01)
*A61B 90/10* (2016.01)

(52) U.S. Cl.
CPC ............ *A61B 90/14* (2016.02); *A61N 1/0539* (2013.01); *A61B 17/844* (2013.01); *A61B 17/864* (2013.01); *A61B 17/8685* (2013.01); *A61B 2090/103* (2016.02)

(58) Field of Classification Search
CPC .... A61B 2017/0453; A61B 2017/0448; A61B 2017/045; A61B 17/0401; A61B 17/844; A61B 17/864; A61B 17/8645
See application file for complete search history.

(56) References Cited

U.S. PATENT DOCUMENTS

| | | | |
|---|---|---|---|
| 6,321,104 | B1 | 11/2001 | Gielen et al. |
| 6,482,182 | B1 | 11/2002 | Carroll et al. |
| 7,588,587 | B2 * | 9/2009 | Barbieri ............ A61B 17/0401 |
| | | | 606/232 |
| 9,161,788 | B2 | 10/2015 | Daubs et al. |
| 9,226,735 | B2 | 1/2016 | Pretre et al. |
| 9,604,052 | B2 | 3/2017 | Behymer et al. |
| 10,265,107 | B2 | 4/2019 | Philippon |
| 2006/0276841 | A1 | 12/2006 | Barbieri |
| 2009/0192546 | A1 * | 7/2009 | Schmieding ....... A61B 17/0401 |
| | | | 606/232 |
| 2011/0166606 | A1 | 7/2011 | Stihl et al. |
| 2012/0271365 | A1 | 10/2012 | Daubs et al. |
| 2014/0155860 | A1 | 6/2014 | Behymer et al. |
| 2014/0343563 | A1 | 11/2014 | Pretre et al. |

* cited by examiner

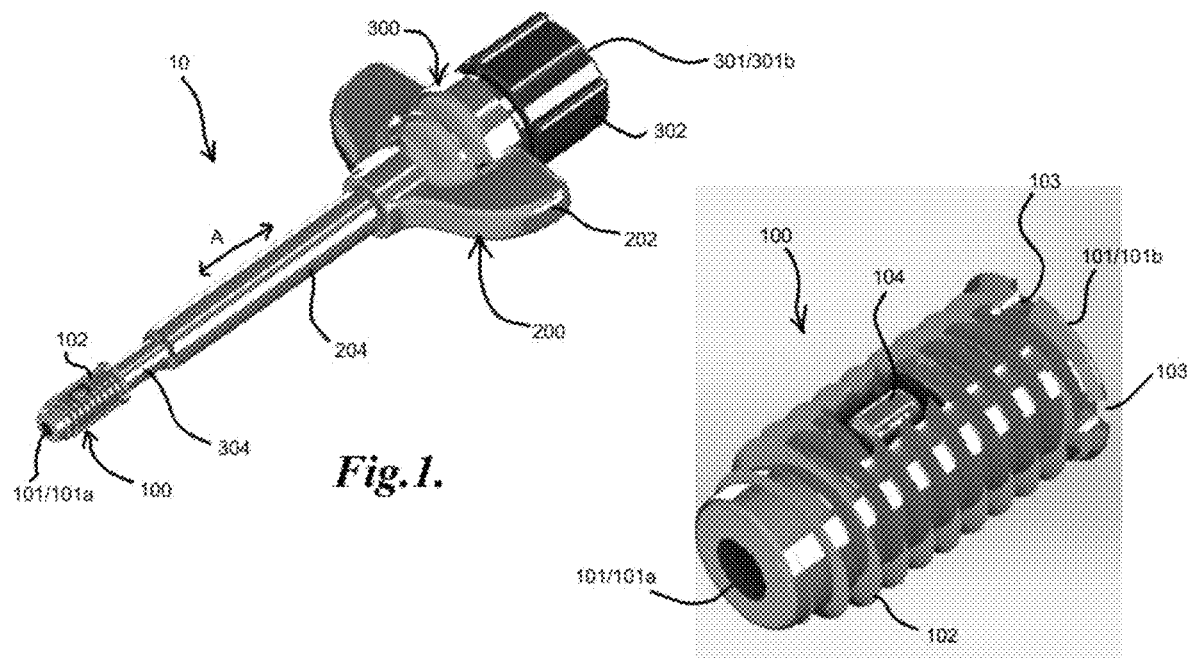
Fig.1.
Fig.1a.
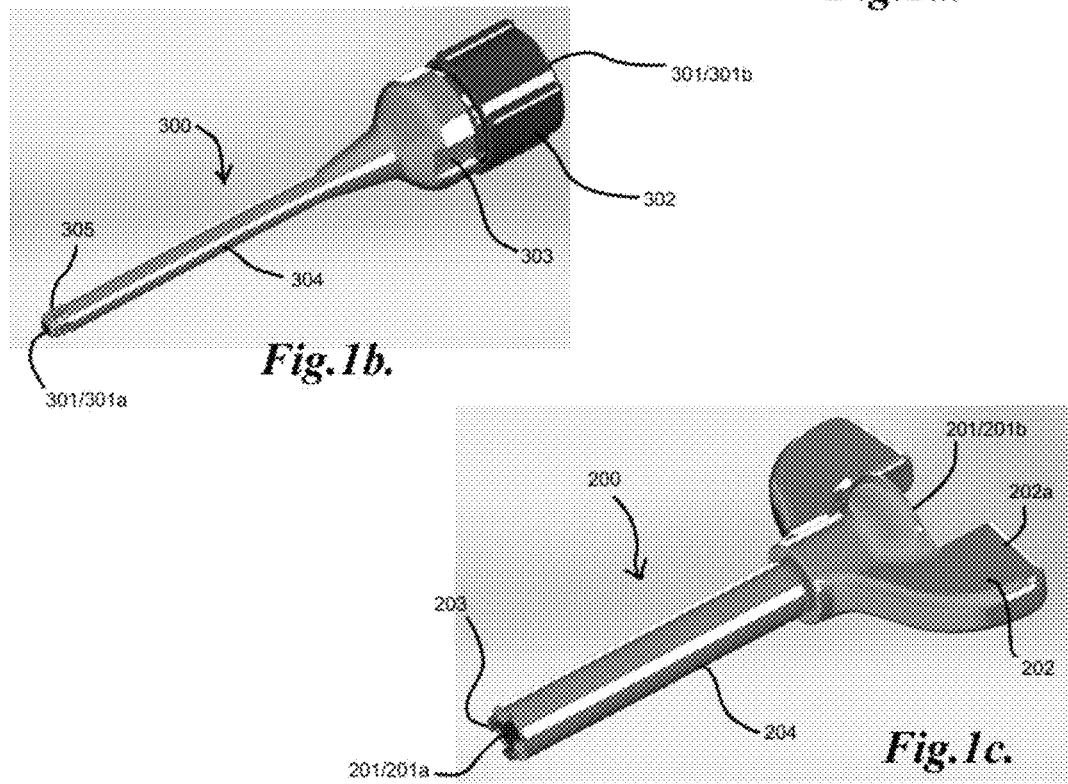
Fig.1b.
Fig.1c.

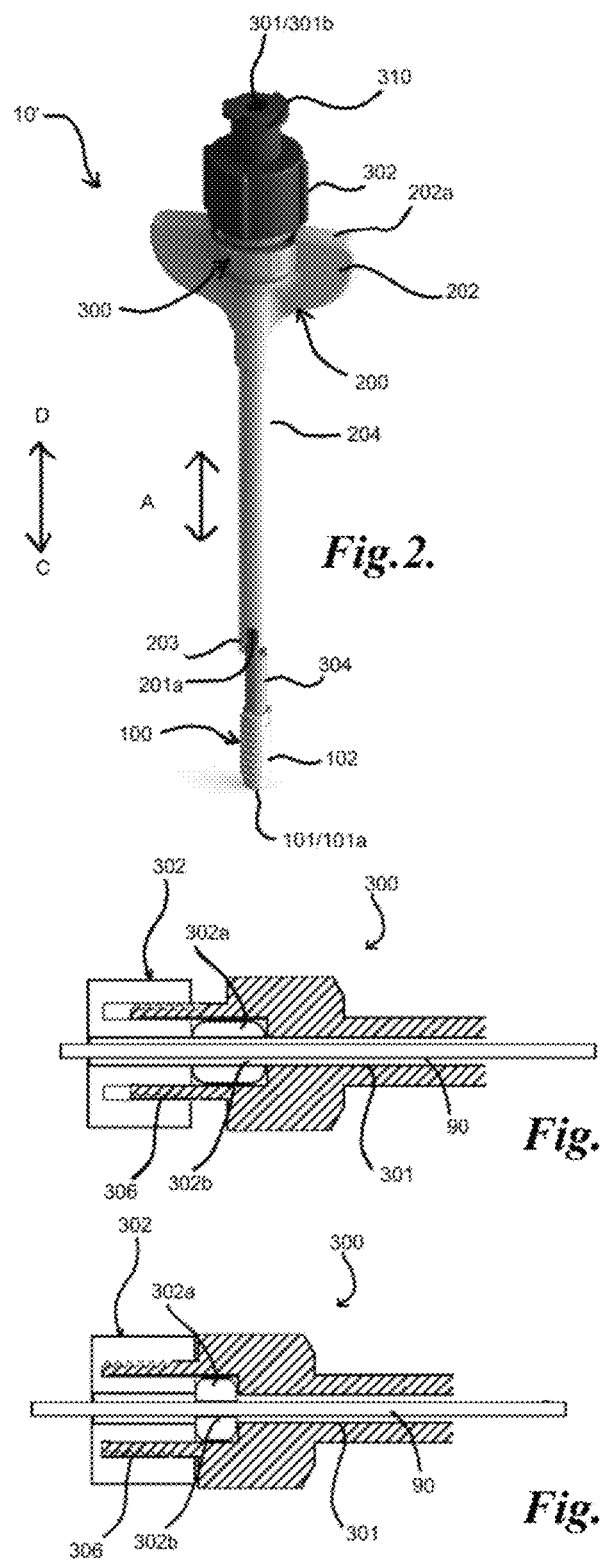
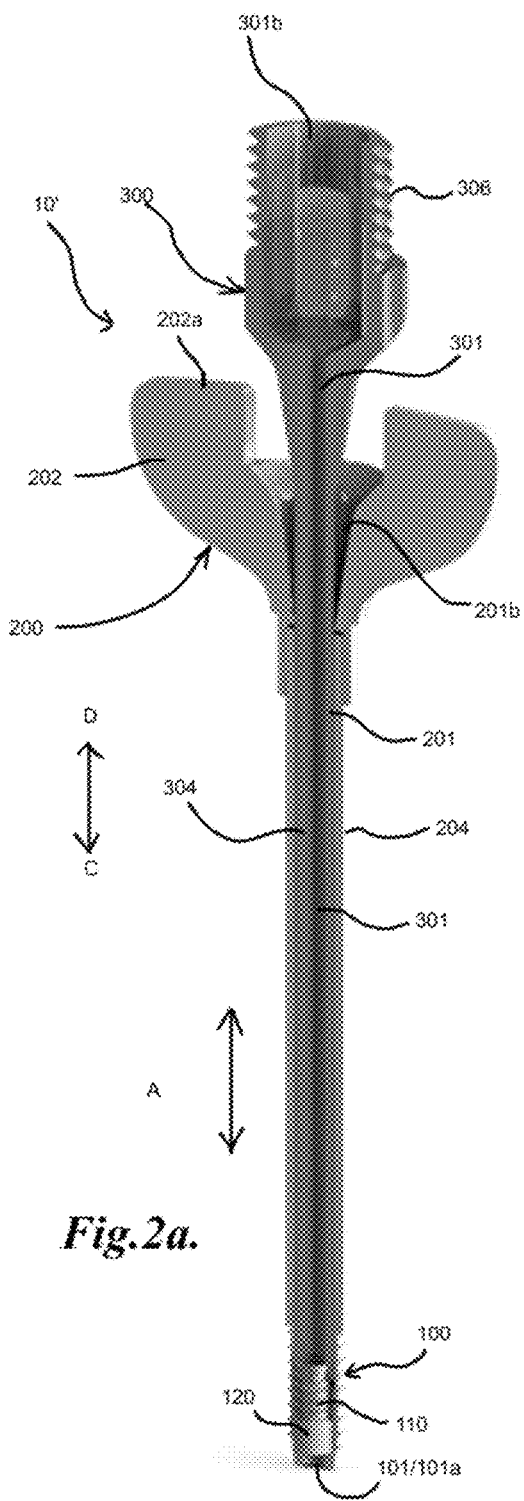
Fig.2.
Fig.1d.
Fig.1e.
Fig.2a.

METHODS AND DEVICES FOR MEDICAL DEVICE PLACEMENT

CROSS-REFERENCE TO RELATED APPLICATIONS

This application is a 371 national stage application of Patent Cooperation Treaty International Application Ser No. PCT/US2017/056387, which claims the benefit and priority of U.S. provisional patent application Ser. No. 62/407,472, filed Oct. 12, 2016, and entitled "BURR-HOLE COVER WITH ELECTRODE CLIP", the contents of all of which are hereby incorporated by reference in their entirety.

FIELD OF THE INVENTION

The present invention relates to methods and devices for placement and retention of medical devices, particularly to methods and devices for placement and retention of medical devices in entry points into a body cavity, and more particularly to methods and devices for placement and retention of electrodes and other devices into body cavities through apertures such as burr holes or twist drill holes in the skull.

COPYRIGHT NOTICE

A portion of the disclosure of this patent document contains material which is subject to copyright protection. The copyright owner has no objection to the facsimile reproduction by anyone of the patent document or the patent disclosure, as it appears in the U.S. Patent and Trademark Office patent file or records, but otherwise reserves all copyright rights whatsoever.

BACKGROUND OF THE INVENTION

In cases where an item such as an electrode is emanating from a drilled skull hole, it is desirable to have a component system that can both cover this drilled hole and secure the exiting electrode or catheter. Current technology relies upon laborious, technically complex constructs that require building a "tower," with precise placement of the electrode, then securing using a combination of a screwed-in clear plastic base with a snapped-on "cap" (e.g. the IGN system acquired by Medtronic).

A method of securing precisely placed electrodes generally incorporate certain qualities: (1) not cause deviation of the precisely placed electrode (placed using other means), hence maintaining a channel for such placement; (2) be able to cover a portion of the hole; (3) be able to have an independent, low-profile system able to be independently tightened and secured for permanent placement as an implant (while any other higher-profile components used in the process of this implant are disengaged).

Two systems which have similar characteristics of both a burr hole cover and securing an electrode presently exist in filings: (1) the IGN Navigus (now owned by Medtronic) and (2) the NeuroPace system.

SUMMARY OF THE INVENTION

The present invention relates to methods and devices for placement and retention of medical devices, particularly to methods and devices for placement and retention of medical devices in entry points into a body cavity, and more particularly to methods and devices for placement and retention of electrodes and other devices into body cavities through apertures such as burr holes or twist drill holes in the skull. In general, a device may be utilized for placement and/or placement of a medical device through an aperture into a body cavity, such as through a burr hole, twist drill hole or similar aperture into a cavity such as the interior of the skull. The device may generally include a channel for introduction of a medical device and at least one holding feature for retaining the medical device in a desired position relative to the body cavity.

In one aspect of the invention, a device for introducing and/or retaining a medical device through an aperture into a body cavity may generally include a base which interfaces and fixes into the aperture, such as a burr hole or twist drill hole through the skull, a sleeve which interfaces with the base and includes a channel through which a medical device is introduced into the base, and an actuator which interfaces with the sleeve and/or the base for altering the position and/or other state, such as placement into the aperture, interfacing of the sleeve with the base and/or changing the retention state of the medical device passing through the sleeve and/or base. The base, sleeve and actuator may generally all include a channel which, when the device is assembled, either form a continuous channel and/or form concentric channels, such as with the channel formed by the base and sleeve being concentric with the channel of the actuator. A medical device for use with the device may include, but is not limited to, an electrode (e.g. for detecting electrical signals from the brain or for delivering electrical signals), catheter, needle, probe, biopsy collector, fiber, and/or any other appropriate medical device. In general, medical devices for use with the device, without limitation, may be filament, fiber, or wire-like such that they may enter and be guided through the channel of the device into an aperture and to a desired target.

In a further aspect of the invention, the base of the device may include a plurality of features and structures for fixing to an aperture into a body cavity, such as a burr hole or twist drill hole into a skull, for holding a medical device in a channel of the base and/or for interfacing with other portions of the device for actuating the holding feature/structure and/or for actuating the base into/out of the aperture.

In some embodiments of the invention, the base includes interfaces for fixing into an aperture into a body cavity such as a burr hole or twist drill hole through a skull, which may generally include screw threads and/or or similar interface features such that the base may be secured to the material around the aperture, such as the bone of the skull. At least a portion of the base may also include features for aiding insertion and/or fixing into the bone, such as tapering (e.g. for aiding in securely wedging into the aperture), sharp edges (e.g. for cutting into the bone), and/or any other appropriate features to aid insertion/fixing. The interface may generally be present at a distal portion and/or more of the base, such as long substantially the entire base.

In some embodiments, the base may further include at least one feature for retaining a medical device in the channel of the base, such as a feature which may be actuated to grasp the medical device in the channel. For example, flanges may be included which may press inward in the channel when the base is driven a certain depth into the aperture. In another example, a Tuohy-Borst or similar fitting may be utilized. In some embodiments, the base includes at least one retaining member within its channel. The at least one retaining member may be, for example, an o-ring or other deformable sealing member. The retaining member may generally be ring-shaped and includes a central aperture through which a medical device may be inserted.

The retaining member is generally adapted to deform in response to compressive axial loads such that the aperture constricts or otherwise decreases in effective size. This may allow the retaining member to securely retain a medical device in the aperture by constricting thereon. The base may generally include an interface which may be actuated to axially compress (or decompress) the retaining member, such as by interfacing with the sleeve such that actuating the sleeve causes axial compression (or decompression) of the retaining member. The interface may, for example, be present at the proximal end of the base.

In some embodiments, the base may also include at least one interface for interacting with an actuator such that the base may be secured to (or backed out of) the aperture, such as, for example, by rotating to screw into (or out of) the bone around the aperture. The interface may include, for example, notches, splines, tabs and/or other similar interface features such that the actuator with corresponding features may interlock with and actuate the base, such as by rotation. The interface may generally be present at the proximal end of the base.

In another aspect of the invention, the sleeve of the device may include a plurality of features and structures for holding a medical device in a channel of the sleeve and/or for interfacing with other portions of the device for actuating/fixing the sleeve relative to the base and/or for interfacing with an actuator. The sleeve may further include a span section which may create spacing between the proximal and distal ends of the sleeve, such that the proximal end is situated at a distance away from the base/aperture for ease of handling/use.

In some embodiments, a sleeve may also be included in the device for interfacing with the base and/or actuator. In general, the sleeve may include a channel therethrough which aligns with the channel in the base to form a continuous channel. The sleeve may further include features for interfacing with the base, such as threads, friction or close fittings, notches, tabs, splines and/or other attachment features which may interact with corresponding features on the base, such as to keep the sleeve in a fixed orientation with the base and/or to couple the sleeve to a retaining feature, such as a Tuohy-Borst fitting or other fitting, such that the sleeve may actuate the retaining feature to hold (or release) a medical device in the channel. The interface may generally be present at the distal end of the sleeve.

In some embodiments, the sleeve may further include a retention feature for securing a medical device in the channel. The retention feature may generally be present at the proximal end of the sleeve, such that, for example, it may be more easily accessed and/or actuated by a user. The retention feature may include a fitting, such as a Tuohy-Borst fitting or other fitting, such that the sleeve may be utilized to hold (or release) a medical device in the channel.

In some embodiments, the sleeve may also include features for interfacing with an actuator such that the actuator may be utilized to actuate the sleeve, such as by rotating the sleeve to attach to the base and/or to rotate the sleeve to actuate a portion of the base, such as the retaining feature of base.

In another aspect of the invention, the actuator of the device may include a plurality of features and structures for interfacing with other portions of the device for actuating/fixing the sleeve relative to the base and/or for interfacing with the base to secure or back out the base from the aperture. The actuator may further include a span section which may create spacing between the proximal and distal ends of the sleeve, such that the proximal end is situated at a distance away from the base/aperture for ease of handling/use. In some embodiments, the span section of the actuator may generally be shorter than the span section of the sleeve such that the actuator may slide along the span section of the sleeve which may be within the channel of the actuator. This may be desirable to change positions of the actuator, such as between interfacing with the sleeve and interfacing with the base. The actuator may then be utilized for both functions independently.

In some embodiments, the actuator may act as a screwdriver or similar device where features of the actuator interface with corresponding features of the base and/or sleeve such that actuating the actuator, such as by rotating it, may cause corresponding actuation of the base and/or sleeve, as appropriate. The actuator may, for example, include threads, splines, notches, tabs and/or other features which may mate or otherwise interact with corresponding features on the base and/or sleeve. The actuator may further include handling features which may aid in grasping and/or rotating the actuator, such as handles, flanges, friction areas, splines, and/or any other appropriate handling feature.

In yet another aspect of the invention, the device may further include a driver which may be utilized to control the insertion of a medical device into the channel of the device. In some embodiments, the driver may include a linear actuator which may grasp and/or otherwise act on the medical device to translate it linearly into/out of the channel. For example, gears or other structures may be utilized to frictionally or otherwise contact the medical device to drive it in or out of the channel, such as in a highly controlled manner. The driver may, for example, be adapted and/or selected for small linear increments to aid in accurate placement of a medical device at a certain depth. The driver may also, for example, register the linear displacement and/or output it to a display for the user to view. The driver may further, for example, be attached to the device, such as to the sleeve with an interface, such that the driver is coupled to the device for fixed positioning of the various components.

In still a further aspect of the invention, the device may be utilized in methods for placing and/or altering the position of medical devices in a body cavity, such as placing/altering the position of electrodes in the brain through a skull aperture, such as a burr hole or twist drill hole.

In some embodiments, the base of the device may be placed into an aperture into a body cavity, such as a burr hole or twist drill hole through the skull. The base may be placed by driving it into the aperture, such as by rotating it with an actuator such that the threads engage the material around the aperture (e.g. bone) to place the base at a desired depth. The sleeve may be fixed to the base, such as by threading onto the base and/or otherwise utilizing the interface features, and the actuator may further placed onto the sleeve (e.g. on the span section), such that it may be utilized to actuate the base, such as to drive it into the aperture, and/or to actuate the sleeve to attach it to the base. A medical device, such as an electrode, may be passed through the channel in the sleeve into the channel of the base to a desired depth. A driver may be utilized to control the advancing/retracting of the medical device in the channel. The medical device may be retained in a certain position by utilizing the retaining feature of the sleeve, such as for temporary placement to verify the correct position. The medical device may also be retained in a position by actuating the retaining feature of the base, such as with the sleeve and/or actuator. The sleeve and/or actuator may then be removed to leave the secured medical device with the base.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. Note that the features illustrated in the drawings are not necessarily drawn to scale.

FIG. 1 illustrates an embodiment of a device for placing a medical device into an aperture with a base, sleeve and actuator;

FIG. 1a illustrates an embodiment of a base of the device;

FIG. 1b illustrates an embodiment of a sleeve of the device;

FIG. 1c illustrates an embodiment of an actuator of the device;

FIGS. 1d and 1e illustrate operation of a Tuohy-Borst type fitting to retain a medical device in a channel of the device;

FIG. 2 illustrates an embodiment of a device for placing a medical device into an aperture with a base, sleeve and actuator with alternative embodiments of interfaces;

FIGS. 2a and 2b show partial cross-sectional views of the device of FIG. 2;

DETAILED DESCRIPTION OF THE INVENTION

Figure 2B:
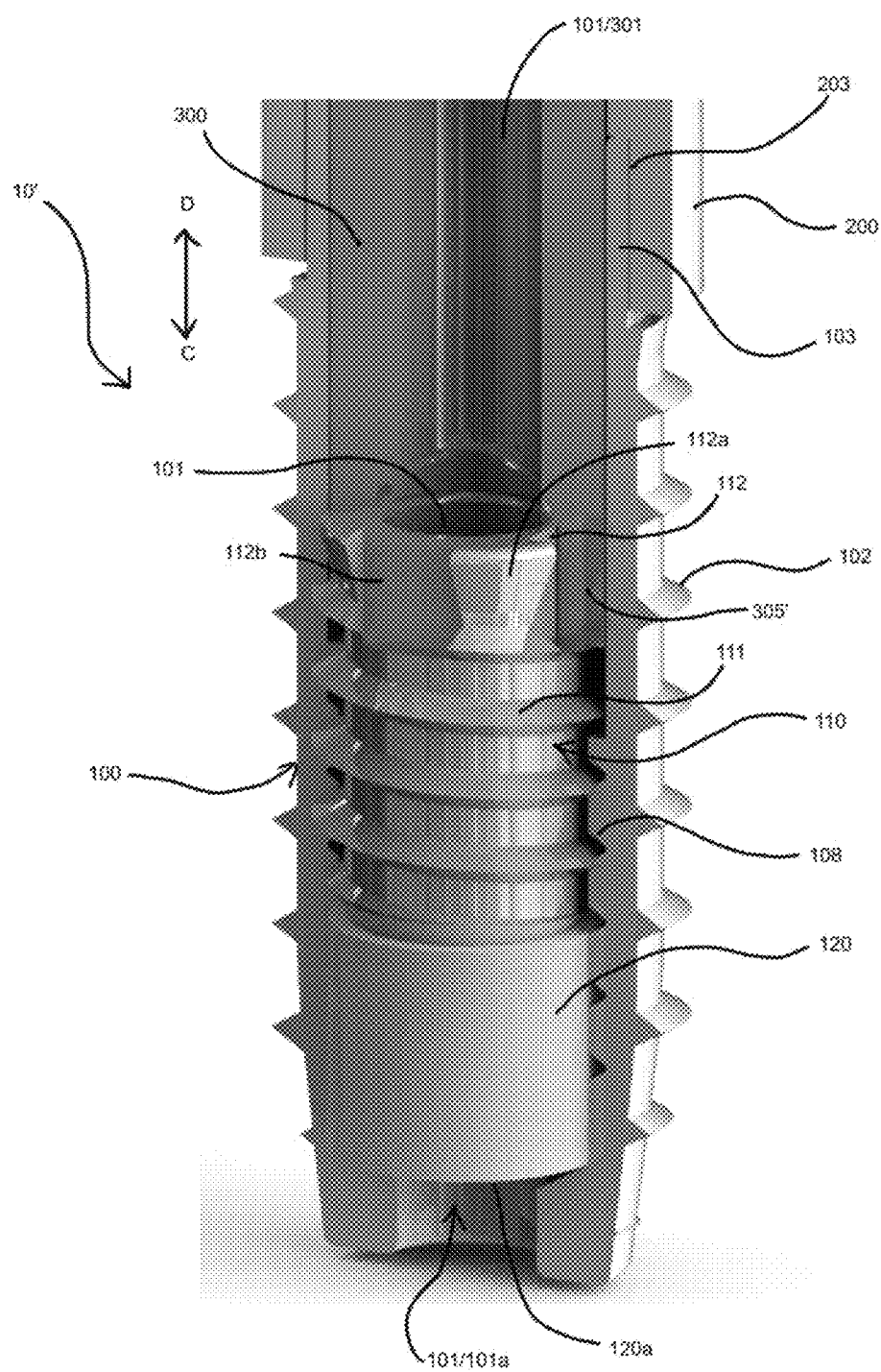

The detailed description set forth below is intended as a description of the presently exemplified methods, devices and compositions provided in accordance with aspects of the present invention, and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention relates to methods and devices for placement and retention of medical devices, particularly to methods and devices for placement and retention of medical devices in entry points into a body cavity, and more particularly to methods and devices for placement and retention of electrodes and other devices into body cavities through apertures such as burr holes or twist drill holes in the skull. In general, a device may be utilized for placement and/or placement of a medical device through an aperture into a body cavity, such as through a burr hole, twist drill hole or similar aperture into a cavity such as the interior of the skull. The device may generally include a channel for introduction of a medical device and at least one holding feature for retaining the medical device in a desired position relative to the body cavity.

In general, the various components of the device may be made from appropriate materials, such as polymers, metals, composites, and/or any other appropriate material or combinations thereof. Suitable polymers may include, but are not limited to, polyethylene; polypropylene; polybutylene; polystyrene; polyester; polytetrafluoroethylene (PTFE); acrylic polymers; polyvinylchloride; Acetal polymers such as polyoxymethylene or Delrin (available from DuPont Company); natural or synthetic rubber; polyamide, or other high temperature polymers such as polyetherimide like ULTEM®, a polymeric alloy such as Xenoy® resin, which is a composite of polycarbonate and polybutyleneterephthalate, Lexan® plastic, which is a copolymer of polycarbonate and isophthalate terephthalate resorcinol resin (all available from GE Plastics); liquid crystal polymers, such as an aromatic polyester or an aromatic polyester amide containing, as a constituent, at least one compound selected from the group consisting of an aromatic hydroxycarboxylic acid (such as hydroxybenzoate (rigid monomer), hydroxynaphthoate (flexible monomer), an aromatic hydroxyamine and an aromatic diamine, (exemplified in U.S. Pat. Nos. 6,242,063, 6,274,242, 6,643,552 and 6,797,198, the contents of which are incorporated herein by reference), polyesterimide anhydrides with terminal anhydride group or lateral anhydrides (exemplified in U.S. Pat. No. 6,730,377, the content of which is incorporated herein by reference) or combinations thereof. Some of these materials are recyclable or may be made to be recyclable. Compostable or biodegradable materials may also be used and may include any biodegradable or biocompostable polyesters such as a polylactic acid resin (comprising L-lactic acid and D-lactic acid) and polyglycolic acid (PGA), polyhydroxyvalerate/hydroxybutyrate resin (PHBV) (copolymer of 3-hydroxy butyric acid and 3-hydroxy pentanoic acid (3-hydroxy valeric acid) and polyhydroxyalkanoate (PHA) copolymers, and polyester/urethane resin. Some non-compostable or non-biodegradable materials may also be made compostable or biodegradable by the addition of certain additives, for example, any oxo-biodegradable additive such as D2W™ supplied by (Symphony Environmental, Borehamwood, United Kingdom) and TDPA® manufactured by EPI Environmental Products Inc. Vancouver, British Columbia, Canada. Compostable or biodegradable materials may also be desirable for disposable versions or portions of the device.

In addition, any polymeric composite such as engineering prepregs or composites, which are polymers filled with pigments, carbon particles, silica, glass fibers, or mixtures thereof may also be used. For example, a blend of polycarbonate and ABS (Acrylonitrile Butadiene Styrene) may be used for the housing. For further example, carbon-fiber and/or glass-fiber reinforced plastic may also be used.

Useful metals or metallic materials may include metal and metal alloys such as aluminum, steel, stainless steel, nickel titanium alloys, shape memory alloys and so on.

In general, for certain applications which involve imaging, the device may be made from magnetic resonance imaging (MRI) compatible or X-ray/computerized tomography (CT) compatible materials, such as polymers, titanium, aluminum, etc.

In one aspect of the invention, a device for introducing and/or retaining a medical device through an aperture into a body cavity may generally include a base, a sleeve and/or an actuator, as illustrated in FIG. 1 with device 10 and in FIG. 2 with a variation of the device 10', with base 100, actuator 200 and sleeve 300. Generally, the device and/or its components may include a distal end toward direction C and a proximal end toward direction D. The base 100 may which interfaces and fixes into the aperture, such as a burr hole or twist drill hole through the skull, a sleeve 300 which interfaces with the base 100 and includes a channel 301 through which a medical device is introduced into the base 100, and an actuator 200 which interfaces with the sleeve 300 and/or the base 100 for altering the position and/or other state, such as placement into the aperture, interfacing of the sleeve 300 with the base 100 and/or changing the retention state of the medical device passing through the sleeve 300 and/or base 100. The base 100, sleeve 300 and actuator 200 may generally all include a channel which, when the device is assembled, either form a continuous channel and/or form concentric channels, such as with the channel formed by the base 100 and sleeve 300 being concentric with the channel of the actuator 200, as illustrated in FIGS. 1, 1a, 1b, 1c, 2 and 2a with channels 101, 201 and 301 of the base 100, actuator 200 and sleeve 300, respectively. The channels 101, 201 and 301 may further include distal openings 101a, 201a, 301a towards direction C and proximal openings 101b, 201b, 301b towards direction D. The base 100 may further be appropriately sized for the size of the aperture being used, such as a burr hole (e.g. generally about 14 mm in diameter) or a twist drill hole (e.g. generally about 3 mm in diameter). In general, utilization of smaller apertures may be desirable, such as an approximately 3 mm twist drill hole, as to reduce the invasiveness and other associated risks with larger openings, and as such the device of the present invention may be desirable for such procedures by utilizing a base 100 that is sized to utilize an approximately 3 mm twist drill hole as an entry aperture, with the sleeve 300 and actuator 200 being also appropriately sized to fit the size constraints of a small aperture.

In a further aspect of the invention, the base of the device may include a plurality of features and structures for fixing to an aperture into a body cavity, such as a burr hole or twist drill hole into a skull, for holding a medical device in a channel of the base and/or for interfacing with other portions of the device for actuating the holding feature/structure and/or for actuating the base into/out of the aperture.

In some embodiments of the invention, the base includes interfaces for fixing into an aperture into a body cavity such as a burr hole or twist drill hole through a skull, which may generally include screw threads and/or similar interface features such that the base may be secured to the material around the aperture, such as the bone of the skull. FIGS. 1, 1a, 2 and 2b illustrate embodiments of a base 100 with interfacing features, shown as threads 102, which may engage and hold onto the material around an aperture, such as bone. At least a portion of the base 100 may also include features for aiding insertion and/or fixing into the bone, such as tapering (e.g. for aiding in securely wedging into the aperture), sharp edges (e.g. for cutting into the bone), and/or any other appropriate features to aid insertion/fixing. FIGS. 1a and 2b illustrate the tapering toward the distal opening 101a of the channel 101. The interface, such as the threads 102, may generally be present at a distal portion and/or more of the base 100, such as long substantially the entire base 100.

In some embodiments, the base may further include at least one feature for retaining a medical device in the channel of the base, such as a feature which may be actuated to grasp the medical device in the channel. For example, flanges may be included which may press inward in the channel when the base is driven a certain depth into the aperture. FIG. 1a illustrates an embodiment of the base 100 with retaining features 104 which extend outward from the surface of the base 100. When the base 100 is inserted into an aperture sufficiently to reach the retaining features 104, they may generally be pushed inward into the channel 101 where they may abut a medical device in the channel 101 to hold it in place.

In another example, as illustrated in FIGS. 2 and 2a, a Tuohy-Borst or similar fitting may be utilized in the base 100. In some embodiments, the base includes at least one retaining member within its channel. The at least one retaining member may be, for example, an o-ring or other deformable sealing member. The retaining member may generally be ring-shaped and includes a central aperture through which a medical device may be inserted. In general, the retaining member may be compressible and/or deformable and may be made from an appropriate material, such as, for example, elastomeric polymers (e.g. silicone, natural or synthetic rubbers, etc.).

FIGS. 2a and 2b show a retaining member 120 with a channel 120a (which is coextensive with channel 101), where the retaining member 120 is subject to loading from a loading member, shown as inner screw 110. The retaining member 120 is generally adapted to deform in response to compressive axial loads such that the aperture (channel 120a) constricts or otherwise decreases in effective size. This may allow the retaining member 120 to securely retain a medical device in the channel 120a by constricting thereon. The base 100 may generally include an interface which may be actuated to axially compress (or decompress) the retaining member 120, such as by interfacing with the sleeve 300 such that actuating the sleeve 300 causes axial compression (or decompression) of the retaining member 120. The interface may, for example, be present at the proximal end of the base 100, as illustrated with inner screw actuating interface 112 which may interface with corresponding inner screw interface 305' of sleeve 300. The interface may include, for example, notches, tabs, splines and/or other similar interface features such that the actuator with corresponding features may interlock with and actuate the base, such as by rotation. As illustrated in FIG. 2b, the inner screw interface 305' may include splines which nest into notches 112b and may then press on splines 112a when the sleeve 300 is rotated to cause rotation of inner screw 110. The rotation may then push the inner screw 110 toward the distal direction C, such as view threading of threads 111 on the inner threads 108 of base 100 to compress retaining member 120. The force of the threading interaction may generally hold in place to maintain the level of compression of the retaining member 120 to hold a medical device in place in the channel 120a.

In some embodiments, the base may also include at least one interface for interacting with an actuator such that the base may be secured to (or backed out of) the aperture, such as, for example, by rotating to screw into (or out of) the bone around the aperture. As illustrated in FIGS. 1a and 1c, an actuation interface 203 on actuator 200 may mate or otherwise interface with actuation interface 103 on base 100. The interface may include, for example, notches, tabs, splines and/or other similar interface features such that the actuator with corresponding features may interlock with and actuate the base, such as by rotation. As illustrated, the interface may include actuation interface 203 (protrusions) may fit into actuation interface 103 (notches) to lock the actuator 200 and base 100 together such that rotating the actuator 200 may rotate the base 100. The interface may generally be present at the proximal end of the base. For example, rotating of the actuator 200 in one direction may generally cause the base 100 to thread into an aperture while rotating the opposite direction may generally cause it back out of the aperture.

In another aspect of the invention, the sleeve of the device may include a plurality of features and structures for holding a medical device in a channel of the sleeve and/or for interfacing with other portions of the device for actuating/fixing the sleeve relative to the base and/or for interfacing with an actuator.

In general, as illustrated in FIGS. 1, 1b, 2 and 2a, the sleeve may further include a span section which may create spacing between the proximal and distal ends of the sleeve, such that the proximal end is situated at a distance away from the base/aperture for ease of handling/use, as shown with span section 304 of sleeve 300.

In some embodiments, a sleeve may also be included in the device for interfacing with the base and/or actuator. In general, the sleeve may include a channel therethrough which aligns with the channel in the base to form a continuous channel, as illustrated in FIGS. 2a and 2b with channels 101 and 301 of base 100 and sleeve 300, respectively. The sleeve 300 may further include features for interfacing with the base, such as threads, friction or close fittings, notches, tabs, splines and/or other attachment features which may interact with corresponding features on the base 100, such as to keep the sleeve in a fixed orientation with the base 100. FIG. 1b shows interface 305 which may couple to corresponding features on base 100, such as internal threads (not shown) threading with the interface 305 (shown as threads). FIG. 2b illustrates the sleeve 300 being retained in the channel 101 of the base 100 and/or interfacing by the interaction of the inner screw interface 305', which may include splines which nest into notches 112b and splines 112a.

The sleeve 300 may also include features or structures to couple the sleeve 300 to a retaining feature, such as a Tuohy-Borst fitting or other fitting, such that the sleeve may actuate the retaining feature to hold (or release) a medical device in the channel. The interface may generally be present at the distal end of the sleeve. The interface may, for example, be present at the distal end of the sleeve 300, as illustrated with inner screw interface 305' of sleeve 300 interfacing with inner screw actuating interface 112 of the inner screw 110 of base 100. The interface may include, for example, notches, tabs, splines and/or other similar interface features such that the actuator with corresponding features may interlock with and actuate the base, such as by rotation. As illustrated in FIG. 2b, the inner screw interface 305' may include splines which nest into notches 112b and may then press on splines 112a when the sleeve 300 is rotated to cause rotation of inner screw 110. The rotation may then push the inner screw 110 toward the distal direction C, such as view threading of threads 111 on the inner threads 108 of base 100 to compress retaining member 120. The force of the threading interaction may generally hold in place to maintain the level of compression of the retaining member 120 to hold a medical device in place in the channel 120a.

In some embodiments, the sleeve may further include a retention feature for securing a medical device in the channel. The retention feature may generally be present at the proximal end of the sleeve, such that, for example, it may be more easily accessed and/or actuated by a user. The retention feature may include a fitting, such as a Tuohy-Borst fitting or other fitting, such that the sleeve may be utilized to hold (or release) a medical device in the channel. FIGS. 1, 1b, 1d, 1e and 2 illustrate a retaining feature, shown as retaining cap 302, which may be at the end of the sleeve 300 towards distal direction D. As illustrated, the retaining cap 302 may be threaded onto or off of threads 306 of sleeve 300 to cause the retaining cap 302 to translate in directions C and D. As shown in FIGS. 1d and 1e, screwing the retaining cap 302 onto the threads 306 may generally cause axial translation of the retaining cap 302 (from FIG. 1d to FIG. 1e), which may generally compress a retaining member 302a with a channel 302b. A medical device, as shown with medical device 90 in channel 301, may be retained in a position when the channel 302b is constricted due to the compression of retaining member 302a.

In some embodiments, the sleeve 300 may also include features for interfacing with an actuator such that the actuator may be utilized to actuate the sleeve, such as by rotating the sleeve to attach to the base and/or to rotate the sleeve to actuate a portion of the base, such as the retaining feature of base. FIGS. 1, 1b, 1c, 2 and 2a illustrate the interfacing of an actuator 200 with the sleeve 300. As shown, sleeve 300 may include interface features 303 which may interface with actuation features 202a on an actuator 200, such that rotation of the actuator 200 may cause corresponding rotation of the sleeve 300. The interface may include, for example, notches, splines, tabs and/or other similar interface features such that the actuator 200 with corresponding features may interlock with and actuate the sleeve 300, such as by rotation. As shown in FIGS. 1 and 2, actuation features 202a (shown as tabs) may interface with the interface features 303 (shown as notches).

In another aspect of the invention, the actuator 200 of the device may include a plurality of features and structures for interfacing with other portions of the device for actuating/fixing the sleeve relative to the base and/or for interfacing with the base to secure or back out the base from the aperture.

As illustrated in FIGS. 1, 1c, 2 and 2a, the actuator 200 may further include a span section 204 which may create spacing between the proximal and distal ends of the sleeve 300, such that the proximal end is situated at a distance away from the base/aperture for ease of handling/use. In some embodiments, as shown in FIGS. 1, 2 and 2a, the span section 204 of the actuator 200 may generally be shorter than the span section 304 of the sleeve 300 such that the actuator 200 may slide along the span section 304 of the sleeve 300 which may be within the channel 201 of the actuator 200, as shown with the actuator 200 sliding A between a proximal position, as shown in FIGS. 1 and 2 with actuator 200 interfacing with the sleeve 300, and a distal position, as shown in FIG. 2a with actuator 200 interfacing with the base 100. This may be desirable to change positions of the actuator 200, such as between interfacing with the sleeve 300 and interfacing with the base 100. The actuator 200 may then be utilized for both functions independently.

In some embodiments, the actuator 200 may act as a screwdriver or similar device where features of the actuator 200 interface with corresponding features of the base 100 and/or sleeve 300 such that actuating the actuator 200, such as by rotating it, may cause corresponding actuation of the base 100 and/or sleeve 300, as appropriate. The actuator 200 may, for example, include threads, splines, notches, tabs and/or other features which may mate or otherwise interact with corresponding features on the base 100 and/or sleeve 300.

As illustrated in FIGS. 1a and 1c, an actuation interface 203 on actuator 200 may mate or otherwise interface with actuation interface 103 on base 100. As illustrated, the interface may include actuation interface 203 (protrusions) may fit into actuation interface 103 (notches) to lock the actuator 200 and base 100 together such that rotating the actuator 200 may rotate the base 100. The interface may generally be present at the proximal end of the actuator 200. For example, rotating of the actuator 200 in one direction may generally cause the base 100 to thread into an aperture while rotating the opposite direction may generally cause it back out of the aperture.

FIGS. 1, 1b, 1c, 2 and 2a illustrate the interfacing of an actuator 200 with the sleeve 300. As shown, actuation features 202a on the actuator 200 may couple with interface features 303 of the sleeve 300, such that rotation of the actuator 200 may cause corresponding rotation of the sleeve 300. As shown in FIGS. 1 and 2, actuation features 202a (shown as tabs) may interface with the interface features 303 (shown as notches).

The actuator 200 may further include handling features which may aid in grasping and/or rotating the actuator, such as handles, flanges, friction areas, splines, and/or any other appropriate handling feature. FIGS. 1, 1c, 2 and 2a illustrate handling features 202 on actuator 200, shown as handles which may further, for example, include actuation features 202a to interface with the interface features 303 of the sleeve as discussed above when the actuator 200 is in the proximal position, as shown in FIGS. 1 and 2.

Figure 3:
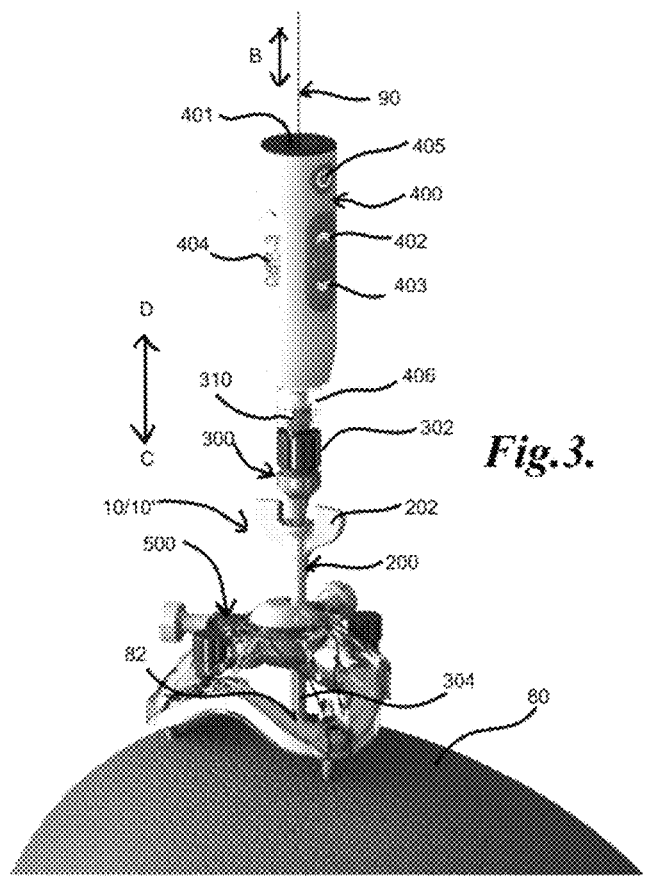
FIG. 3 illustrates an assembly of the device of FIG. 2, a medical device, a driver and a stereotactic guide to a human skull.
Figure 3A:
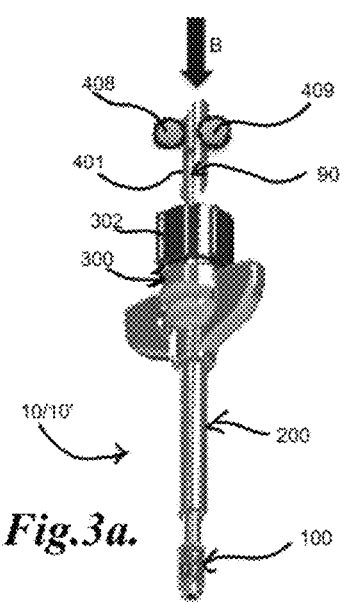
FIGS. 3a and 3b illustrate a microgear drive mechanism in the driver to advance/retract the medical device in the channel of the device.
Figure 3B:
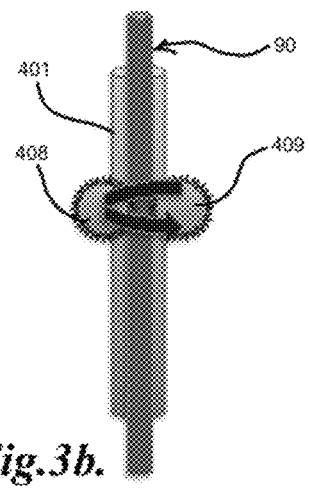

In yet another aspect of the invention, the device may further include a driver which may be utilized to control the insertion of a medical device into the channel of the device. FIGS. 3, 3a and 3b illustrate the use of a driver 400 with the device 10/10'.

In some embodiments, the driver 400 may include a linear actuator which may grasp and/or otherwise act on the medical device to translate it linearly into/out of the channel. For example, gears or other structures may be utilized to frictionally or otherwise contact the medical device to drive it in or out of the channel, such as in a highly controlled manner. FIGS. 3a and 3b illustrate a linear actuator with translating actuators, such as gears 408, 409, which act on a medical device 90 in a channel 401 of the driver 400 to translate the medical device 90 back and forth in direction B into the channel 101/301 of the device 10/10'. In some embodiments, the gears 408, 409 may be calibrated such that each given rotation fraction of the gears may translate into a known distance of linear movement of the medical device 90. The gears 408, 409 may generally be driven by a motor or other rotational source.

The driver 400 may, for example, be adapted and/or selected for small linear increments to aid in accurate placement of a medical device at a certain depth. The driver may also, for example, register the linear displacement and/or output it to a display for the user to view. A microdriver device may include, for example, Microdrive devices (available from FHC, Inc.), which include features for tracking depth of a medical device (e.g. an electrode), such as on the sub-millimeter level and may operate in manual (e.g. by the user actuating the controls) or automatic (e.g. to a set depth) modes. The drive 400 may, for example, include controls and display features, such as illustrated in FIG. 3 with power control 405, reverse and forward controls 402, 403, and display 404, which may, for example, display the depth of advancement. The driver 400 may also include a tare function to zero out the depth at the option of the user. The driver 400 may also, for example, include features for outputting display information to a wired or wireless display (e.g. by Bluetooth, WiFi, NFC or other wireless communication).

The driver 400 may further, for example, be attached to the device 10/10', such as to the sleeve 300, with an interface, such that the driver 400 is coupled to the device 10/10' for fixed positioning of the various components. FIGS. 2 and 3 illustrate interface features 310 on the sleeve 300 and interface features 406 on the driver 400, which may include, for example, threads, splines, notches, tabs, Luer locks and/or other features which may mate or otherwise interact with corresponding features.

In still a further aspect of the invention, the device may be utilized in methods for placing and/or altering the position of medical devices in a body cavity, such as placing/altering the position of electrodes in the brain through a skull aperture, such as a burr hole or twist drill hole.

In some embodiments, the base 100 of the device 10 may be placed into an aperture 82 into a body cavity, such as a burr hole or twist drill hole, through the skull 80 as illustrated in FIG. 3. The base 100 may be placed by driving it into the aperture 82, such as a burr hole or twist drill hole, such as by rotating it with an actuator 200 such that the threads 102 engage the material around the aperture 82 (e.g. bone) to place the base 100 at a desired depth. The sleeve 300 may be fixed to the base 100, such as by threading onto the base 100 with threads 305 onto internal threads of the base 100. The actuator 200 may further placed onto the sleeve 300 (e.g. on the span section 304), such that it may be utilized to actuate the base 100, such as to drive it into the aperture 82 while in a distal position, as shown in FIGS. 2a and 3, and/or to actuate the sleeve 300 to attach it to the base 100 while in the proximal position, as shown in FIGS. 1 and 2. A medical device 90, such as an electrode, may be passed through the channel 301 in the sleeve 300 into the channel 101 of the base 100 to a desired depth. A driver 400 may be utilized to control the advancing/retracting of the medical device 90 in the channel 301. The medical device 90 may be retained in a certain position by utilizing the retaining feature of the sleeve 300, such as the retaining cap 302, such as for temporary placement to verify the correct position. The medical device 90 may also be retained in a position by actuating the retaining feature of the base 100, such as by driving the base 100 further into the aperture 82 using the actuator 200 in the distal position. This may, for example, be utilized to push the holding features 104 further in such that they press inward into the channel 101 and press against the medical device 90 to hold it in place. The medical device 90 may be backed up before a given amount to compensate for the additional depth from the base 100 being driven in further. The sleeve 300 and/or actuator 200 may then be removed to leave the secured medical device 90 with the base 100 in the aperture 82. Positioning of the base 100 at a desired position and/or angle may also be facilitated by using a positioning device, such as the stereotactic positioning device 500 as illustrated in FIG. 3.

In some embodiments, the base 100 of the device 10 may be placed into an aperture 82 into a body cavity, such as a burr hole or twist drill hole, through the skull 80 as illustrated in FIG. 3. The base 100 may be placed by driving it into the aperture 82, such as burr hole or twist drill hole, such as by rotating it with an actuator 200 such that the threads 102 engage the material around the aperture 82 (e.g. bone) to place the base 100 at a desired depth. The sleeve 300 may be fixed to the base 100, such as by inserting it into the channel 101 of the base 100 such that the inner screw interface 305' may couple with the inner screw actuation interface 112 of the inner screw 110, as shown in FIG. 2b. The actuator 200 may further placed onto the sleeve 300 (e.g. on the span section 304), such that it may be utilized to actuate the base 100, such as to drive it into the aperture 82 while in a distal position, as shown in FIGS. 2a and 3, and/or to actuate the sleeve 300 to actuate the inner screw 110 while in the proximal position, as shown in FIG. 2. A medical device 90, such as an electrode, may be passed through the channel 301 in the sleeve 300 into the channel 101 of the base 100 to a desired depth. A driver 400 may be utilized to control the advancing/retracting of the medical device 90 in the channel 301. The medical device 90 may be retained in a certain position by utilizing the retaining feature of the sleeve 300, such as the retaining cap 302, such as for temporary placement to verify the correct position. The medical device 90 may also be retained in a position by actuating the retaining feature of the base 100, such as by driving the inner screw 110 to compress the retaining member 120 using the sleeve 300 interacting with the inner screw actuation interface 112. The actuator 200 may also be utilized to turn the sleeve 300 by placing it in the proximal position, as shown in FIG. 2, such that the sleeve interface 202a couples with actuation interface 303. This may, for example, be utilized to constrict the channel 120a to press against the medical device 90 to hold it in place. The sleeve 300 and/or actuator 200 may then be removed to leave the secured medical device 90 with the base 100 in the aperture 82. Positioning of the base 100 at a desired position and/or angle may also be facilitated by using a positioning device, such as the stereotactic positioning device 500 as illustrated in FIG. 3.

EXAMPLE 1 OF DEVICE WORKFLOW

An example of a method for placing a medical device, such as an electrode, utilizing the device 10 may generally be utilized, for example, to place an electrode at a desired depth in a human brain, such as to reach a desired structure or region to measure and/or deliver electrical signals. The following steps may be employed:
1. Mark skin using navigation (for entry point)—the mark may be made using a stereotactic guide, such as a frameless or framed stereotactic system;
2. Make an incision at the entry point; Make incision such that drill hole will not directly overlie drilled hole, slightly anterior to the hole, such as about 1" in a non-linear fashion;
3. Use small self-retaining thumbscrew retractor to open the incision as desired; Use frame or frameless system to drill a hole under navigation guidance;
4. Pierce dura with a needle, such as an 18-gauge needle, and irrigate using normal saline, until eluent clear of any blood or bone dust;
5. Screw in sleeve 300 into base 100;
6. Screw in base 100 into drilled hole 82 using the actuator 200 in the distal position;
7. Place the base 100 by screwing into skull until the lower portion is screwed in (i.e. none of the protruding holding features 104 are screwed in);
8. Place electrode 90 through the channel 301 of the sleeve 300, and tighten the retaining cap 302 to secure electrode 90 in desired position (via a Tuohy mechanism, to perform testing, etc. of patient);
9. After reaching optimal position of electrode 90 (via anatomical or physiological/functional methods, at discretion of surgeon), retreat electrode 90 by a given distance to accommodate the further drilling in of the base 100 to engage the holding features 104, such as by 5 mm;
10. Screw in base 100 further, such as another 2 mm (as the middle portion of the base 100 is larger than 3.2 mm due to tapering, this puts pressure inwardly into the channel 101 whereby the electrode 90 is grasped along the inner portion of the middle segment of the base 100);
11. Screw in the upper portion of the base 100 till practically flush with skull 80;
12. Release the retaining cap 302 (as the electrode 90 should now be held by the holding features 104 of the base 100);
13. Remove the sleeve 300 from base 100 using the actuator 100 in the proximal position engaging the actuation interface 303 of the sleeve 300;
14. The electrode 90 may be manipulated by using a driver 400, which may be coupled to the retaining cap 302 via interface features 310, 406; The depth may be monitored via the display 404 or an external display.

Additional Scenario: if electrode 90 is already implanted and an adjustment or removal effort is being performed, the actuator 200 may be used in isolation without the sleeve 300 to engage the base 100 and turning to loosen or tighten (with room available for exiting electrode 90 over which the actuator 200 engages the actuation interface 103).

EXAMPLE 2 OF DEVICE WORKFLOW

An example of a method for placing a medical device, such as an electrode, utilizing the device 10' may generally be utilized, for example, to place an electrode at a desired depth in a human brain, such as to reach a desired structure or region to measure and/or deliver electrical signals. The following steps may be employed:
1. Mark skin using navigation (for entry point)—the mark may be made using a stereotactic guide, such as a frameless or framed stereotactic system;
2. Make an incision at the entry point; Make incision such that drill hole will not directly overlie drilled hole, slightly anterior to the hole, such as about 1" in a non-linear fashion;
3. Use small self-retaining thumbscrew retractor to open the incision as desired; Use frame or frameless system to drill a hole under navigation guidance;
4. Pierce dura with a needle, such as an 18-gauge needle, and irrigate using normal saline, until eluent clear of any blood or bone dust;
5. Place sleeve 300 into channel 101 of through distal opening 101b of base 100;
6. Screw in base 100 into drilled hole 82 using the actuator 200 in the distal position;
7. Place the base 100 by screwing until upper portion of the base 100 till practically flush with skull 80;
8. Place electrode 90 through the channel 301 of the sleeve 300, and tighten the retaining cap 302 to secure electrode 90 in desired position (via a Tuohy mechanism, to perform testing, etc. of patient);

9. After reaching optimal position of electrode 90 (via anatomical or physiological/functional methods, at discretion of surgeon), secure electrode 90 by engaging the inner screw interface 305' of the sleeve 300 with the inner screw actuation interface 112 and rotating to drive the inner screw 110 down to compress the retaining member 120 until the channel 120a constricts to hold the electrode 90 in place. The actuator 200 may be utilized to facilitate rotating of the sleeve 300 by engaging the sleeve interface 202a with the actuation interface 303 with the actuator 200 in the proximal position, as in FIG. 2;

10. Release the retaining cap 302 (as the electrode 90 should now be held by the retaining member 120 of the base 100);

11. Remove the sleeve 300 from base 100 using the actuator 100 in the proximal position engaging the actuation interface 303 of the sleeve 300;

12. The electrode 90 may be manipulated by using a driver 400, which may be coupled to the retaining cap 302 via interface features 310, 406; The depth may be monitored via the display 404 or an external display.

Additional Scenario: if electrode 90 is already implanted and an adjustment or removal effort is being performed, the actuator 200 may be used in isolation without the sleeve 300 to engage the base 100 and turning to loosen or tighten (with room available for exiting electrode 90 over which the actuator 200 engages the actuation interface 103).

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. A device for manipulating a medical device comprising:

a base having an approximately cylindrical form with proximal and distal ends, external threads, a first retaining feature and a base channel spanning from said proximal end to said distal end of said base;

a sleeve having proximal and distal ends, a span section, a first interface which couples to said base at said distal end of said sleeve, a second interface at said proximal end of said sleeve, a second retaining feature and a sleeve channel spanning from said proximal end to said distal end of said sleeve and being coextensive with said base channel;

an actuator having proximal and distal ends, a span section shorter than said span section of said sleeve, a first interface adapted to couple to said base at said distal end of said actuator, a second interface at said proximal end of said actuator adapted to couple with said second interface of said sleeve and an actuator channel spanning from said proximal end to said distal end of said actuator and being concentric with said span section of said sleeve; wherein said base channel and said sleeve channel are adapted to receive a medical device therethrough, said actuator being translatable along said span section of said sleeve between a first position and a second position, said first position engaging said first interface of said actuator with said base and said second position engaging said second interface of said actuator with said second interface of said sleeve; and an inner screw in said base adapted to compress the first retaining feature when actuated by said first interface of said sleeve.

2. The device of claim 1, wherein said second retaining feature comprises a Tuohy-Borst fitting.

3. The device of claim 1, further comprising a driver adapted to translate said medical device in said base channel.

4. The device of claim 1, further comprising a driver adapted to translate said medical device in said base channel, said driver comprising a microdrive with sub-millimeter control.

5. The device of claim 1, further comprising handle features on said actuator.

6. The device of claim 1, wherein said first interface of said actuator and said base comprise corresponding features selected from the group consisting of splines, notches, depressions, teeth, tabs, threads and friction fittings.

7. The device of claim 1, wherein said second interface of said actuator and said second interface of said sleeve comprise corresponding features selected from the group consisting of splines, notches, depressions, teeth, tabs, threads and friction fittings.

8. The device of claim 1, wherein said base and said second interface of said sleeve comprise corresponding features selected from the group consisting of splines, notches, depressions, teeth, tabs, threads and friction fittings.

9. The device of claim 1, wherein said device is manufactured from magnetic resonance imaging (MRI) or X-ray/computerized tomography (CT) compatible materials.

10. The device of claim 1, wherein said span section of said sleeve passes through said actuator channel such that said actuator may translate between said first and second positions.

11. The device of claim 1, wherein said base is sized to be fixable in an aperture is selected from the group consisting of a burr hole and a twist drill hole.

12. The device of claim 1, wherein said device is sized such that said base is fixable into an approximately 3 mm diameter twist drill hole.

13. The device of claim 1, wherein said first retaining feature is adapted to reversibly retain a medical device in said base channel.

14. The device of claim 1, wherein said second retaining feature being adapted to reversibly retain a medical device in said sleeve channel.

15. The device of claim 1, wherein said actuator channel is outside of said span section of said sleeve.

16. The device of claim 1, wherein said first position engaging said first interface of said actuator with said base is adapted to enable said actuator to rotate in unison with said base to fixate into a tissue, and said second position engaging said second interface of said actuator with said second interface of said sleeve is adapted to enable said actuator to rotate in unison with said sleeve to engage said first retaining feature to reversibly retain said medical device.

\* \* \* \* \*